United States Patent
Yarita

(10) Patent No.: US 6,780,158 B2
(45) Date of Patent: Aug. 24, 2004

(54) SIGNAL PROCESSING METHOD AND PULSE WAVE SIGNAL PROCESSING METHOD

(75) Inventor: Masaru Yarita, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 70 days.

(21) Appl. No.: 10/318,228

(22) Filed: Dec. 13, 2002

(65) Prior Publication Data

US 2003/0120160 A1 Jun. 26, 2003

(30) Foreign Application Priority Data

Dec. 14, 2001 (JP) .................................... P2001-381374

(51) Int. Cl.[7] .............................. A61B 5/02; A61B 6/00; A61B 5/00; G01R 23/00; G01N 33/48
(52) U.S. Cl. ...................... 600/500; 600/476; 600/479; 600/323; 600/310; 702/75; 702/76; 702/40; 702/19; 702/189
(58) Field of Search ................................ 600/500–503, 600/481, 473, 475–477, 479, 300, 309–310, 322–324, 326, 330; 702/1, 19, 40, 46, 50, 74–78, 66, 189

(56) References Cited

U.S. PATENT DOCUMENTS

| | | | |
|---|---|---|---|
| 5,632,272 A | | 5/1997 | Diab et al. |
| 6,081,735 A | * | 6/2000 | Diab et al. .................. 600/336 |
| 6,198,951 B1 | * | 3/2001 | Kosuda et al. .............. 600/323 |
| 6,650,917 B2 | * | 11/2003 | Diab et al. .................. 600/323 |

* cited by examiner

*Primary Examiner*—Mary Beth Jones
*Assistant Examiner*—Navin Natnithithadha
(74) *Attorney, Agent, or Firm*—Sughrue Mion, PLLC

(57) ABSTRACT

A first signal and a second signal are provided as two continuous signals having an identical fundamental frequency. A first spectrum which is either one of a frequency spectrum or a frequency power spectrum of the first signal in a predetermined time period is obtained. A second spectrum which is either one of a frequency spectrum or a frequency power spectrum of the second signal in the predetermined time period is obtained. A normalized value which corresponds a ratio of a difference between the first spectrum and the second spectrum and a sum of the first spectrum and the second spectrum at the fundamental frequency is obtained. A ratio of an amplitude of a signal component of the first signal and an amplitude of a signal component of the second signal is obtained based on the normalized value.

5 Claims, 4 Drawing Sheets

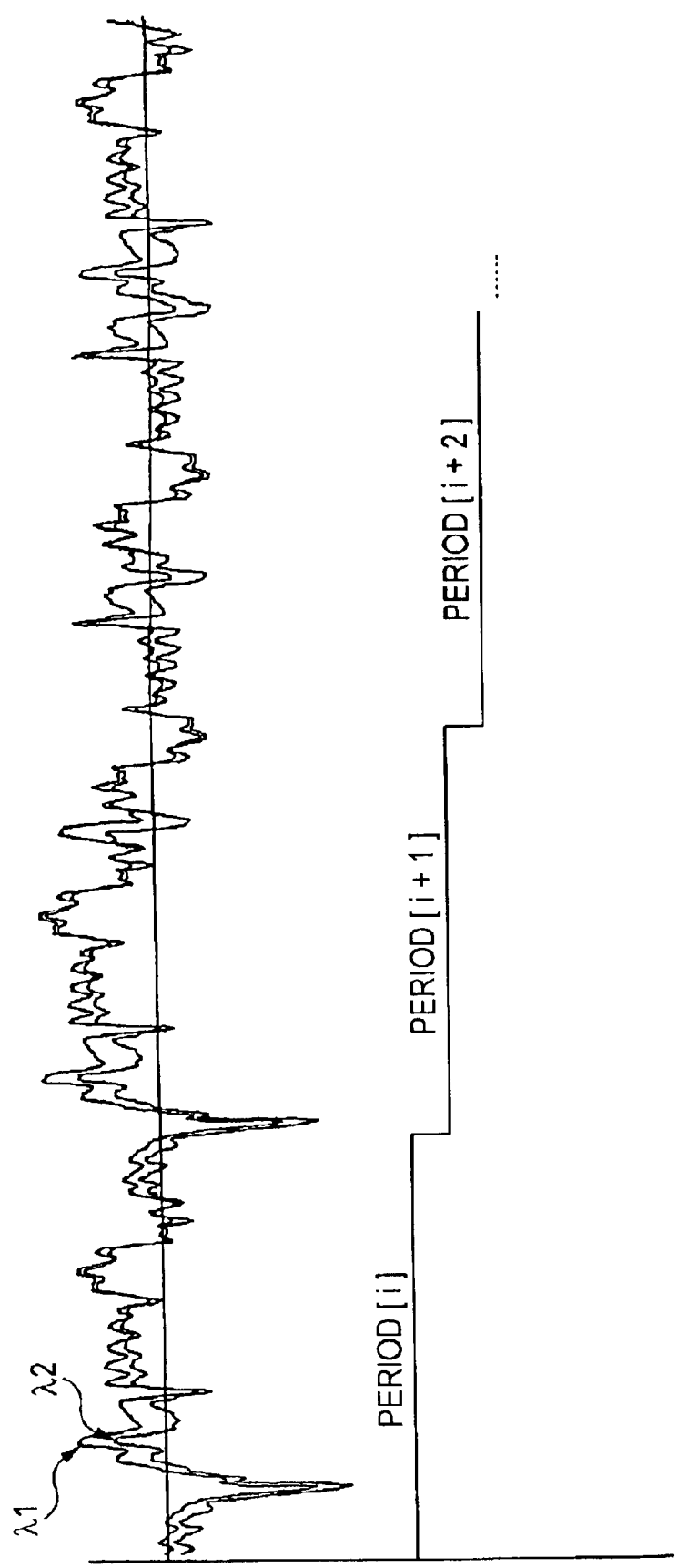

SIGNAL PROCESSING METHOD AND PULSE WAVE SIGNAL PROCESSING METHOD

BACKGROUND OF THE INVENTION

The invention relates to a signal processing method, and more particularly, to elimination of pulse wave noise, which can be used in measuring an oxygen saturation through pulse photometry.

A pulse oximeter has hitherto been used for continuously and noninvasively measuring an oxygen saturation of arterial blood. In the case of the pulse oximeter, a probe is attached to a finger or ear lobe of an examinee, Red light and infrared light, which differ in wavelength from each other, are irradiated from the probe to a living body in the manner of time division. An oxygen saturation S is measured on the basis of a ratio $\Phi$ between pulsation components of light absorbances obtained from transmitted or reflected light of the two different wavelengths. For instance, a wavelength of 660 nm is used for red light, and a wavelength of 940 nm is used for infrared light Two light-emitting diodes for emitting these wavelengths and one light-receiving photodiode are housed in the probe. Provided that a pulsation component of a light absorbance caused by pulsation of infrared light is taken as S1 and a pulsation component of a light absorbance caused by pulsation of red light is taken as S2, the ratio $\Phi$ (hereinafter sometimes called simply an "absorbance ratio $\Phi$") is determined by the following equations.

$$\Phi = S2/S1 \tag{1}$$

$$S = f(\Phi) \tag{2}$$

In such a pulse oximeter, any movement of a patient during measurement will cause noise components to be mixed into a pulse wave to be detected by a probe, thereby hindering accurate measurement of an oxygen saturation S. To prevent such a case, conventionally, attempts have been made to eliminate the influence of such noise.

As described in, e.g., U.S. Pat. No. 5,632,272, pulsation components S1, S2 measured in determining an oxygen saturation are considered to include signal components s1, s2 and noise components n1, n2. There is determined a ratio of s1 to s2 such that a correlation between the signal component s1 and the noise component n1 becomes minimum.

However, in order to determine a ratio of S1 to s2 such that the correlation between the signal component s1 and the noise component n1 becomes minimum, computation must be performed while the value of the ratio is sequentially changed. As a result, the amount of computation becomes enormous, thus imposing considerable computation load on a measurement apparatus. In addition, computation processing takes much time, thus posing a problem on immediate computation.

SUMMARY OF THE INVENTION

It is therefore an object of the invention to reduce the amount of computation and immediately eliminating noise components from a measurement signal. In particular, the invention aims at eliminating noise from a pulse waveform on which noise has been superimposed for reasons of body movement, thereby reproducing an original pulse wave. It is also an object of the invention to provide an apparatus for accurately measuring an oxygen saturation through pulse photometry.

In order to achieve the above objects, according to the invention, there is provided a method of processing two continuous signals having an identical fundamental frequency, comprising the steps of:

providing a first signal and a second signal as the two continuous signals;

obtaining a first spectrum which is either one of a frequency spectrum or a frequency power spectrum of the first signal in a predetermined time period;

obtaining a second spectrum which is either one of a frequency spectrum or a frequency power spectrum of the second signal in the predetermined time period;

obtaining a first normalized value which corresponds a ratio of a difference between the first spectrum and the second spectrum and a sum of the first spectrum and the second spectrum at the fundamental frequency; and obtaining a first ratio of an amplitude of a signal component of the first signal and an amplitude of a signal component of the second signal based on the first normalized value.

With such a method, the above first ratio can be determined even when the first signal and the second signal include noises.

Preferably, the signal processing method further comprises the steps of.

obtaining a second normalized value which corresponds a ratio of a difference between the first spectrum and the second spectrum and a sum of the first spectrum and the second spectrum at a noise fundamental frequency;

obtaining a second ratio of an amplitude of a noise component of the first signal and an amplitude of a noise component of the second signal based on the second normalized value; and eliminating noises from at least one of the first signal and the second signal based on the first ratio and the second ratio.

With such a method, the noise components can be suitably eliminated to determine at least one of the amplitude of the signal component of the first signal and the amplitude of the signal component of the second signal.

Here, it is preferable that the signal processing method further comprises the step of displaying at least one of the first signal and the second signal in which the noises have been eliminated at the noise eliminating step.

In this case, there can be displayed pulse waves where noise components have been suitably eliminated.

Preferably, the first signal and the second signal are provided as data with respect to pulse waves measured by pulse photometry.

In this case, the above first and second ratios can be determined from the first and second signals measured by pulse photometry.

Here, it is preferable that the first signal is data with respect to a pulse wave of infrared light, and the second signal is data with respect to a pulse wave of red light, The signal processing method further comprises the step of obtaining an oxygen saturation based on the first ratio.

With such a method, an oxygen saturation can be measured with superior accuracy.

BRIEF DESCRIPTION OF THE DRAWINGS

The above objects and advantages of the present invention will become more apparent by describing in detail preferred exemplary embodiments thereof with reference to the accompanying drawings, wherein:

FIG. 3 is a view showing a timing chart of processing of the pulse wave signal;

DETAILED DESCRIPTION OF THE PREFERRED EMBODIMENTS

A pulse wave signal processing method serving as a signal processing method of the invention, and one embodiment of a pulse oximeter utilizing the method will be described in detail hereinbelow by reference to the drawings.

Figure 1:
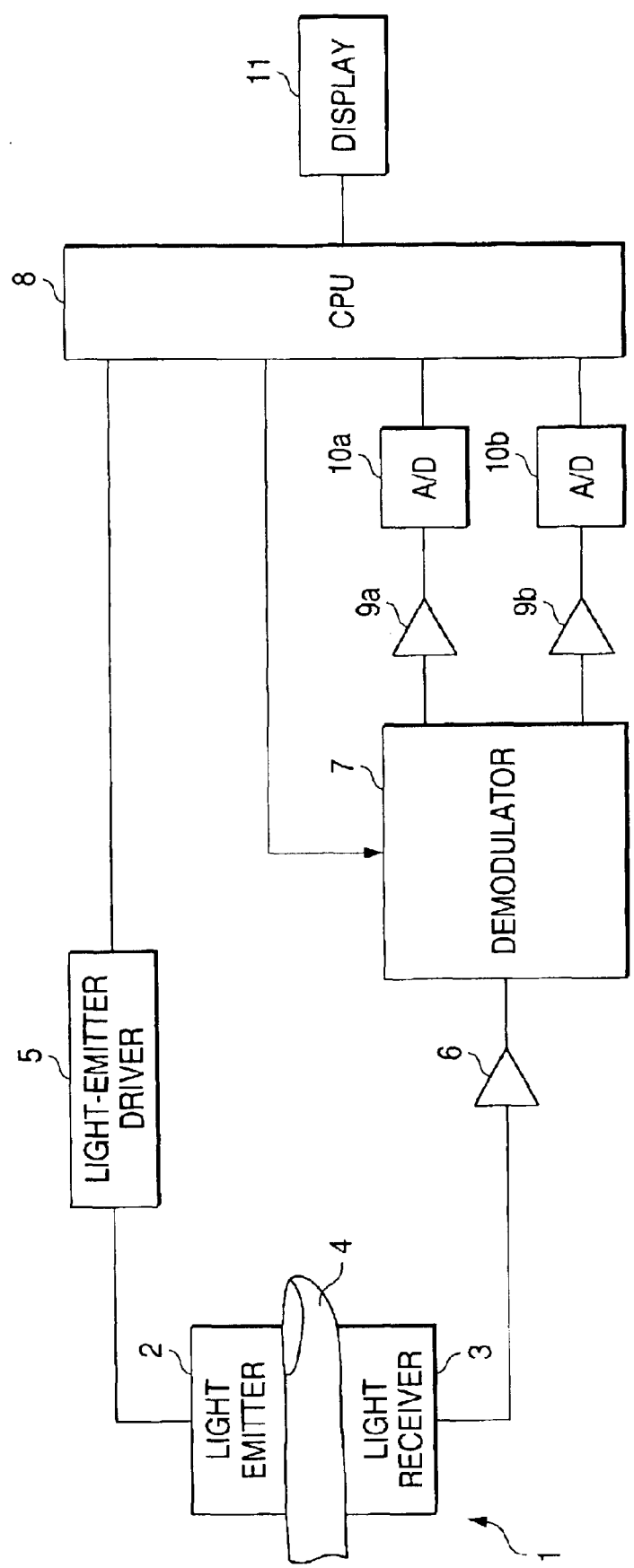
FIG. 1 is a view showing the configuration of an oxygen saturation measurement apparatus of an embodiment which processes a pulse wave signal.

In a pulse oximeter shown in FIG. 1, a probe 1 has a light emitter 2 and a light receiver 3, whereby a fingertip (living tissue) 4 is interposed between the light emitter 2 and the light receiver 3. The light emitter 2 has two light-emitting diodes, one emitting infrared light (having a first wavelength $\lambda 1$; that is, 940 nm) and the other emitting red light (having a second wavelength $\lambda 2$; that is, 660 nm). The light emitter 2 is activated by a light-emitter driver 5, and infrared light and red light are emitted alternately.

The light receiver 3 has a photodiode, receives light which has transmitted through the fingertip, and outputs an electric signal corresponding to the intensity of the transmitted light A signal output from the light receiver 3 is amplified by an amplifier 6, and the thus-amplified signal is demodulated by a demodulator 7. The demodulator 7 separately outputs signals corresponding to infrared light and red light. The signals are amplified by amplifiers 9a, 9b and converted to digital signals by analog-to-digital converters 10a, 10b. The digital signals are input to a central processing unit (CPU) 8.

The CPU 8 controls the demodulator 7 and the light-emitter driver 5 and processes the signals output from the analog-to-digital converters 10a, 10b. Results of processing are output to a display 11.

The results output on the display 11 include the waveform of the pulse wave from which noise has been eliminated, the number of pulse rates, and a value of $SpO_2$ (an oxygen saturation).

Figure 2:
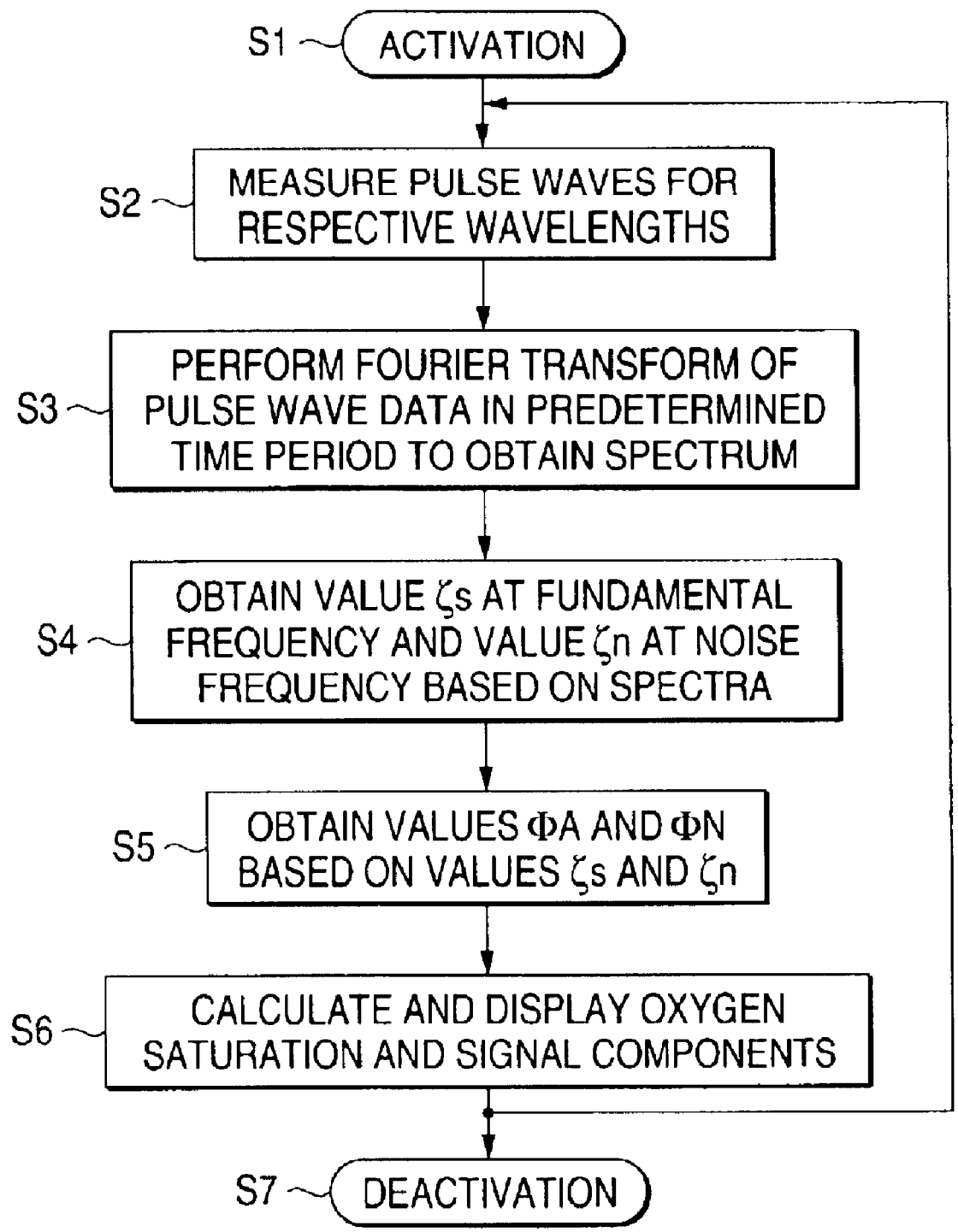
FIG. 2 is a view showing a flowchart of processing of the pulse wave signal.

The invention is characterized by eliminating noise from a pulse wave during the course of signal processing as shown in FIG. 2.

The measurement apparatus is activated in Step S1. Next, as has been described by reference to FIG. 1, a pulse wave of infrared ray IR and that of red light R are measured in Step S2. The thus-measured pulse waves are input to the CPU 8. The waveforms of pulse waves, such as those shown in FIG. 3, are measured with respect to each of the wavelengths $\lambda 1$ and $\lambda 2$.

As mentioned previously, the oxygen saturation S can be computed as a function of the absorbance ratio $\Phi$. First, a ratio of a pulsation component to a direct current component of a pulse wave obtained by infrared light after the light has been transmitted or subjected to reflection is taken as IR, and a ratio of a pulsation component to a direct current component of a pulse wave obtained by red light after the light has been transmitted or subjected to reflection is taken as R. The ratios are approximations of the pulsation component of a light absorbance for each wavelength. Each of the ratios includes a signal component Si stemming from pulsation and noise Ni. Specifically, $$IR = S1 + N1 \tag{3}$$

$$R = S2 + N2 \tag{4}$$

where S1 is an original signal component; N1 is a noise component; S2 is an original signal component; and N2 is a noise component. Here, the following are defined.

$$\Phi A = S2/S1 \tag{5}$$

$$\Phi N = N2/N1 \tag{6}$$

At this time, the following relationship stands between the oxygen saturation S and $\Phi A$.

$$S = f(\Phi A) \tag{7}$$

If the following equation is used in place of Equation (5) while no noise components are eliminated from the pulsation component, a result of computation of an oxygen saturation also includes a measurement error.

$$\Phi = R/IR \tag{8}$$

An attempt is made to transform the above equations. First the following definition is employed for eliminating a signal component from a measured signal, thereby transforming the equation.

$$\begin{aligned} N' &= R - \Phi A \cdot IR \\ &= S2 + N2 - \Phi A(S1 + N1) \\ &= S2 + N2 - \Phi A \cdot S1 - \Phi A \cdot N1 \\ &= (S2 - \Phi A \cdot S1) + (N2 - \Phi A \cdot N1) \end{aligned} \tag{9}$$

Here, $S2 = \Phi A \cdot S1$ is derived from Equation (5). The expression is further transformed as follows.

$$\begin{aligned} N' &= (S2 - S2) + (N2 - \Phi A \cdot N1) \\ &= N2 - \Phi A \cdot N1 \\ &= N1(N2/N1 - \Phi A) \end{aligned}$$

The following equation is derived from Equation (6).

$$N' = N1(\Phi N - \Phi A)$$

Since $N' = R - \Phi A \cdot IR = N1(\Phi N - \Phi A)$, the expression can be transformed as follows.

$$\begin{aligned} N1 &= (R - \Phi A \cdot IR) / (\Phi N - \Phi A) \\ &= N' / (\Phi N - \Phi A) \end{aligned} \tag{10}$$

$$N2 = N1 \cdot \Phi N \tag{11}$$

Description will now be given of obtaining characteristic information about a pulse wave by converting IR, R through Fourier transform and computing an absolute value of a spectrum or a power spectrum.

Figure 4A:
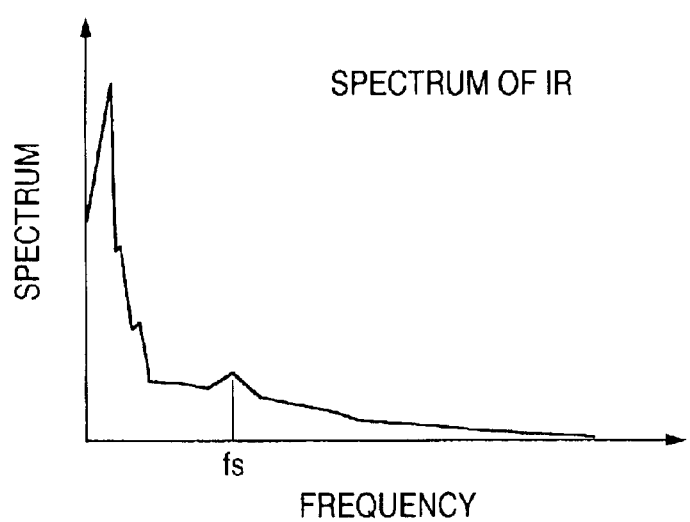
FIG. 4A is a view showing a spectrum of an infrared-light pulse wave.
Figure 4B:
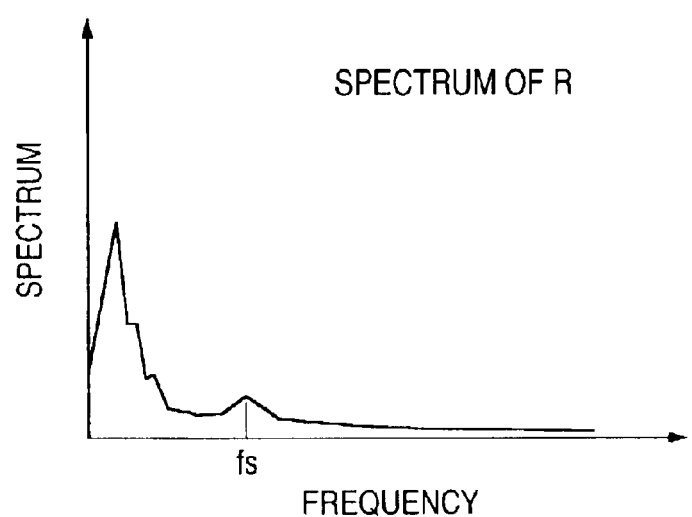
FIG. 4B is a view showing a spectrum of a red-light pulse wave.

The pulse waves for the infrared light (IR) having the first wavelength and the red light (R) having the second wavelength are obtained as shown in FIG. 3. In order to obtain the absolute value of a spectrum or the power spectrum, the Fourier transform is performed for each data sample obtained in every predetermined time period (period [i], period [i+1], period [i+2], ... ). FIG. 4A shows a spectrum (Spc. IR) of infrared light IR, and FIG. 4B shows a spectrum (Spc. R") of red light R.

Figure 5:
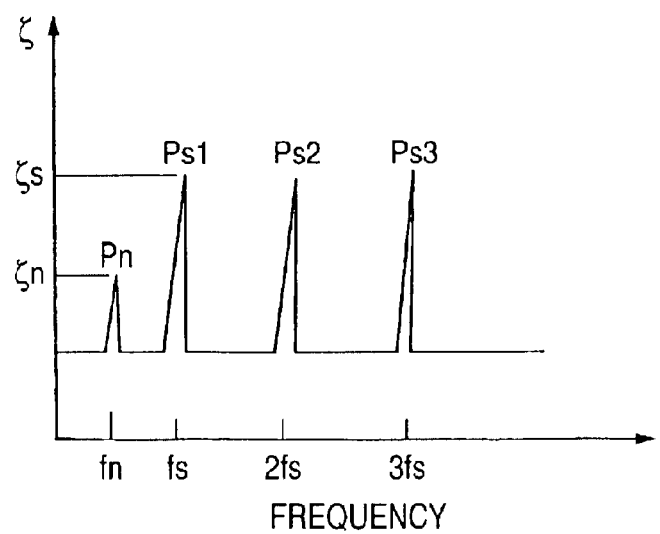
FIG. 5 is a view showing a result of normalization of the spectra.

As a result of the following computation being performed in accordance with a frequency, a graph shown in FIG. 5 is obtained.

$$(\text{Spc. IR} - \text{Spc. R})/(\text{Spc. IR} + \text{Spc. R}) \tag{12}$$

$$[1-(\text{Spc. R}/\text{Spc. IR})]/[1+(\text{Spc. R}/\text{Spc. IR})] \tag{13}$$

Here, (Spc. R/Spc. IR) is considered to be equal to $\Phi$, and hence Equation (13) can also be expressed as follows.

$$(1-\Phi)/(1+\Phi) \tag{14}$$

Consequently, the fundamental frequency fs of a pulse wave is expressed as follows.

$$(1-\Phi A)/(1+A) \tag{15}$$

Further, a noise frequency fn assumes a value expressed as follows.

$$(1-\Phi N)/(1+\Phi N) \tag{16}$$

As shown in FIG. 5, as a result of computation of Equations (12) through (14), a peak Psi appears in the fundamental frequency (corresponding to a heart rate cycle) fs of a pulse wave. The value of the peak Ps1 is taken as $\xi s$. Peaks Ps2, Ps3, ... appear in corresponding frequencies 2fs, 3fs, ... of a higher harmonic of the fundamental frequency fs.

A peak Pn attributable to noise appears in the vicinity of the peak Ps1. The value of the peak Pn is taken as $\xi n$, and the frequency thereof is taken as fn.

From Equation 15, two equations stand as follows.

$$(1-\Phi A)/(1+\Phi A)=\xi s \tag{17}$$

$$\Phi A=(1-\xi s)/(1+\xi s) \tag{18}$$

From Equation 16, two equations stand as follows.

$$(1-\Phi N)/(1+\Phi N)=\xi n \tag{19}$$

$$\Phi N=(1-\xi n)/(1+\xi n) \tag{20}$$

From these equations, $\Phi A$ and $\Phi N$ can be computed.

The oxygen saturation S can be determined directly from Equation (7) through use of $\Phi A$ determined by Equation (18). From Equations (3), (4), (10), and (6), the following equations stand.

$$S1 = IR - N1 \tag{21}$$
$$= IR - (R - \Phi A \cdot IR)/(\Phi N - \Phi A)$$

$$S2 = R - N2 \tag{22}$$
$$= R - N1 \cdot \Phi N$$

The measured IR, R and the computed $\Phi A$, $\Phi N$ are substituted into Equations (21), (22), thereby determining signal components S1, 32. The signal components can be displayed on the display 11.

In Step S3, pulse wave data measured during a predetermined time period are subjected to Fourier transform, thereby computing a spectrum (an absolute value of a spectrum or a power spectrum).

In Step S4, the peak value $\xi s$ of the fundamental frequency and the peak value $\xi n$ of the noise frequency are computed by Equations (15), (16) through use of the spectrum obtained in Step S3.

Next, in Step S5, $\Phi A$ is computed from the value $\xi s$ obtained in Step S4 through use of Equation (18), and $\Phi N$ is computed from the value $\xi n$ obtained in Step S4 through use of Equation (20).

In Step S6, the oxygen saturation S is computed from $\Phi A$ obtained in Step S5 through use of Equation (7). Further, the signal component S1 or S2 of the pulse wave is computed from $\Phi N$ through use of Equation (21) or (22). The oxygen saturation S and the signal component S1 or S2 of the pulse wave are displayed on the display 11. A time period during which data are to be computed is a time period corresponding to the length of data used in Fourier transform (a unit time period; ie., period [i]).

Returning to Step S2, processing pertaining to Steps S2 through S6 is iterated through use of data pertaining to the next time period (a unit time period during which Fourier transform is to be performed; i.e., period [i+1]).

In Step S7, the processing is terminated and the measurement apparatus is deactivated.

Here, the unit period is a period during which no abrupt changes appear in a pulse wave; for example, about six seconds.

The invention is not limited to application to measurement of an oxygen saturation, but can also be applied to measurement of the concentration of light-absorbing material existing in blood.

What is claimed is:

1. A method of processing two continuous signals having an identical fundamental frequency, comprising the steps of:
   providing a first signal and a second signal as the two continuous signals;
   obtaining a first spectrum which is either one of a frequency spectrum or a frequency power spectrum of the first signal in a predetermined time period;
   obtaining a second spectrum which is either one of a frequency spectrum or a frequency power spectrum of the second signal in the predetermined time period;
   obtaining a first normalized value which corresponds a ratio of a difference between the first spectrum and the second spectrum and a sum of the first spectrum and the second spectrum at the fundamental frequency;
   obtaining a first ratio of an amplitude of a signal component of the first signal and an amplitude of a signal component of the second signal based on the first normalized value.

2. The signal processing method as set forth in claim 1, wherein the first signal and the second signal are provided as data with respect to pulse waves measured by pulse photometry.

3. The signal processing method as set forth in claim 2, wherein the first signal is data with respect to a pulse wave of infrared light, and the second signal is data with respect to a pulse wave of red light,
   the method further comprising the step of obtaining an oxygen saturation based on the first ratio.

4. The signal processing method as set forth in claim 1, further comprising the steps of:
   obtaining a second normalized value which corresponds a ratio of a difference between the first spectrum and the second spectrum and a sum of the first spectrum and the second spectrum at a noise fundamental frequency;

obtaining a second ratio of an amplitude of a noise component of the first signal and an amplitude of a noise component of the second signal based on the second normalized value; and eliminating noises from at least one of the first signal and the second signal based on the first ratio and the second ratio.

5. The signal processing method as set forth in claim 4, further comprising the step of displaying at least one of the first signal and the second signal in which the noises have been eliminated at the noise eliminating step.

* * * * *

UNITED STATES PATENT AND TRADEMARK OFFICE
CERTIFICATE OF CORRECTION

PATENT NO. : 6,780,158 B2
DATED : August 24, 2004
INVENTOR(S) : Masaru Yarita

It is certified that error appears in the above-identified patent and that said Letters Patent is hereby corrected as shown below:

Column 5,
Line 18, equation 15, change "$(1-\Phi A)/(1+A)$" to -- $(1-\Phi A)/(1+\Phi A)$ --.

Signed and Sealed this

Twenty-second Day of February, 2005

JON W. DUDAS
*Director of the United States Patent and Trademark Office*